United States Patent [19]

Anderson et al.

[11] 4,076,714

[45] Feb. 28, 1978

[54] 1-METHYL-4-(2-CARBOXY-THIOXANTHEN-9-YLIDENE)-PIPERIDINE AN APPETITE STIMULANT AND ANTIHISTAMINIC AGENT

[75] Inventors: Paul S. Anderson, Lansdale; David C. Remy, North Wales, both of Pa.

[73] Assignee: Merck & Co., Inc., Rahway, N.J.

[21] Appl. No.: 626,899

[22] Filed: Oct. 29, 1975

Related U.S. Application Data

[63] Continuation-in-part of Ser. No. 526,483, Nov. 25, 1974, abandoned.

[51] Int. Cl.$^2$ ............... A61K 31/445; C07D 211/06; C07D 275/00
[52] U.S. Cl. ............................ 424/267; 260/293.51; 260/293.57
[58] Field of Search ................. 424/267; 260/293.57, 260/293.51

[56] References Cited

U.S. PATENT DOCUMENTS

| | | | |
|---|---|---|---|
| 2,996,503 | 8/1961 | Sprague et al. | 424/267 X |
| 3,055,903 | 9/1962 | Renz et al. | 260/293.44 |
| 3,116,291 | 12/1963 | Peterson et al. | 260/328 |
| 3,275,640 | 9/1966 | Engelhardt et al. | 260/293.4 |

*Primary Examiner*—Jerome D. Goldberg
*Assistant Examiner*—Daren M. Stephens
*Attorney, Agent, or Firm*—William H. Nicholson; Harry E. Westlake, Jr.

[57] ABSTRACT

1-Methyl-4-(2-carboxy-thioxanthen-9-ylidene)-piperidine is disclosed to have pharmaceutical utility as an appetite stimulant and an antihistamine with low antiserotonin and anticholinergic activity. Also disclosed are processes for the preparation of such compound; pharmaceutical compositions comprising such compound; and methods of treatment comprising administering such compound and compositions.

3 Claims, No Drawings

1-METHYL-4-(2-CARBOXY-THIOXANTHEN-9-YLIDENE)-PIPERIDINE AN APPETITE STIMULANT AND ANTIHISTAMINIC AGENT

This is a continuation-in-part of Application Serial No. 526,483, filed November 25, 1974, now abandoned.

BACKGROUND OF THE INVENTION

This invention relates to 1-methyl-4-(2-carboxythioxanthen-9-ylidene)piperidine as an appetite stimulant and antihistamine with low antiserotonin and anticholinergic activity for the treatment of histaminically induced allergies; also contemplated within the scope of the present invention are pharmaceutically acceptable salt; ester and amide derivatives thereof. Further, this invention relates to processes for the preparation of such compounds; to pharmaceutical compositions comprising such compounds; and to methods of treatment comprising administering such compounds and compositions when an appetite stimulant or antihistamine is indicated. The free acid form of the 1-methyl-4-(2-carboxy-thioxanthen-9-ylidene)piperidine of the present invention has the following structural formula (I):

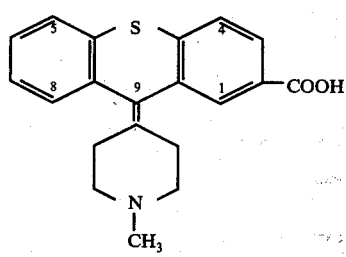

Accordingly, it is an object of the present invention to provide 1-methyl-4-(2-carboxy-thioxanthen-9-ylidene)piperidine and its pharmaceutically acceptable salt, ester and amide derivatives as appetite stimulants and antihistamines. It is a further object of this invention to provide processes for the preparation of such compounds; pharmaceutical compositions comprising such compounds; and methods of treatment comprising administering such compounds and compositions when an appetite stimulating or antihistaminic effect is indicated.

DETAILED DESCRIPTION OF THE INVENTION

The compounds of the present invention may conveniently be prepared from 2-bromo-thioxanthen-9-one [see 24 Journal of Organic Chemistry 1914 (1959) and U.S. Pat. No. 3,275,640 (September 27, 1966), incorporated herein by reference, for disclosure of said 2-bromo-thioxanthen-9-one and 1-methyl-4-(2-bromothioxanthen-9-ylidene)piperidine] by reaction with 1-methyl-4-piperidylmagnesium halide in a suitable solvent such as tetrahydrofuran and the like to provide 1-methyl-4-(2-bromo-9-hydroxy-9-thioxanthyl)piperidine, which is dehydrated on treatment with a suitable dehydrating agent such as a mineral acid and the like to provide 1-methyl-4-(2-bromothioxanthen-9-ylidene)-piperidine, which on conversion to the 2-cyano species by treatment with cuprous cyanide followed by hydrolysis yields the desire 1-methyl-4-(2-carboxy-thioxanthen-9-ylidene)piperidine of the present invention. The following diagram illustrates this process:

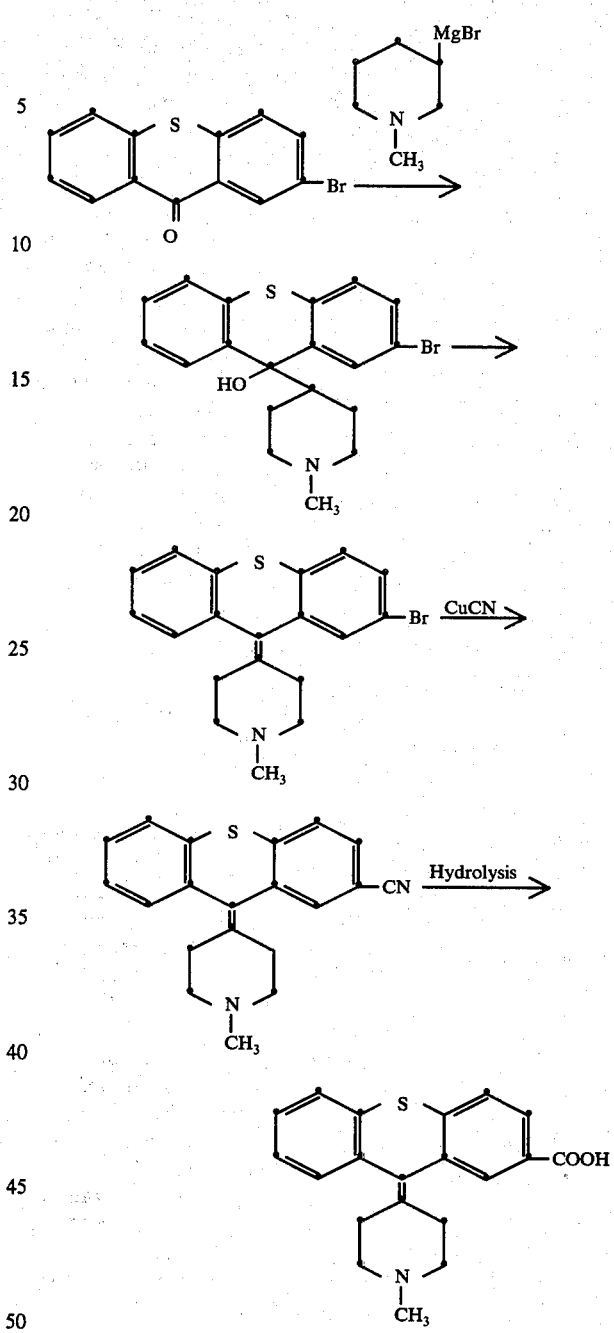

Suitable pharmaceutical salt, ester and amide forms of the 1-methyl-4-(2-carboxy-thioxanthen-9-ylidene)-piperidine of the present invention may be prepared by conventional means. Salt forms are the most preferred and include (relative to the nitrogen atom of the piperidyl moiety): the hydrochloride, sulfate, phosphate, citrate, tartrate, succinate and the like; with respect to salts based upon the carboxy function, salts derived from the alkali and alkaline earth metals such as sodium and potassium are preferred. These salts are generally equivalent in potency to the free acid form taking into consideration the stoichiometric quantities employed.

In the method of treatment and pharmaceutical composition aspects of the present invention it is noted that the precise unit dosage form and dosage level depend upon the case history of the individual being treated and consequently are left to the discretion of the therapist.

In general, however, the compounds of the present invention produce the desired effect of appetite stimulation or antihistaminic action when given at from about 0.01 to about 10.0 mg. per kg. body weight per day and preferably about 0.1–1 mg./kg. body weight per day. The preferred form of delivery of the instant compounds for appetite stimulation of domestic animals is by solution in drinking water or preformulated feedstuffs. For human and animal administration, any of the usual pharmaceutical oral forms may be employed such as tablets, elixirs and aqueous suspensions comprising from about 0.01 to about 10.0 mg. of the compounds of this invention per kg. body weight given daily. Thus, for example, tablets given 2–4 time per day comprising from about 0.5 to about 50 mg. of the compounds of this invention are suitable for human treatment. Sterile solutions (representatively given for human treatment) for injection comprising from about 0.1 to about 10.0 mg. of the compounds of this invention given two to four times daily are also suitable means of delivery.

The following examples representatively illustrate but do not limit the product, compositional or method of treatment aspect of the present invention.

EXAMPLE 1

Preparation of 1-methyl-4-(2-carboxy-thioxanthen-9-ylidene)piperidine

A mixture of 0.035 mole of 1-methyl-4-(2-bromothioxanthen-9-ylidene)piperidine, 8.8 g. (0.098 mole) of cuprous cyanide and 100 ml. of hexamethylphosphoramide is stirred and heated at 180° C for 10 hours. To the cooled solution is added 100 ml. of a saturated aqueous solution of sodium cyanide, 100 ml. of water, and 100 ml. of benzene. After stirring, the mixture separates into two phases. The aqueous phase is removed and extracted with two 100 ml. portions of benzene. All of the benzene phases are combined and washed with 100 ml. portion of: a saturated aqueous solution of sodium cyanide, a 0.1M aqueous solution of sodium cyanide, and water. After drying over magnesium sulfate, the solution is filtered and the benzene is removed on a rotatory evaporator. On triturating with acetonitrile, the residue crystallizes. The material is collected by filtration, washed with acetonitrile, and dried to give 6.44 g. (61%) of 1-methyl-4-(2-cyano-thioxanthen-9-ylidene)-piperidine that is homogeneous by thin layer chromotography. A mixture of 3.0 g. of 1-methyl-4-(2-cyano-thioxanthen-9-ylidene)-piperidine and 100 ml. of 6N hydrochloric acid is stirred and refluxed for 24 hours. The hydrochloric acid is removed on a rotatory evaporator at 80° C. The residue is dissolved in water and made basic by the addition of 5% sodium hydroxide. After filtering, the solution is made acidic by the addition of glacial acetic acid. The solution is concentrated on a rotatory evaporator and as the acetic acid is removed the product crystallizes. This product is removed by filtration and washed with hot water, cold water, and finally with absolute ethanol. The product is dried at 100° C. in high vacuum for 36 hours to give 1-methyl-4-(2-carboxy-thioxanthen-9-ylidene)piperidine, melting point 319°–323° C.

Analysis Calc. for: $C_{20}H_{19}NO_2S$. Calc.: C, 71.19; H, 5.68; N, 4.15; F, 9.50. Found: C, 70.84; H, 5.87; N, 4.62; F, 9.30.

The hydrochloride salt is prepared by the addition of 6N HCl to a saturated ethanolic solution of the above-prepared 1-methyl-4-(2-carboxy-thioxanthen-9-ylidene)-piperidine. The resulting precipitate is collected, washed with ethanol and recrystallized from absolute ethanol to provide 1-methyl-4-(2-carboxy-thioxanthen-9-ylidene)-piperidine hydrochloride.

EXAMPLE 2

Pharmaceutical compositions

A typical tablet containing 1 mg. 1-methyl-4-(2-carboxy-thioxanthen-9-ylidene)piperidine per tablet is prepared by mixing together with the active ingredient calcium phosphate, lactose and starch in the amounts shown in the tables below. After these ingredients are thoroughly mixed, the appropriate amount of magnesium stearate is added and the dry mixture blended for an additional three minutes. This mixture is then compressed into tablets weighing approximately 124 mg. each. Similarly prepared are tablets containing 1-methyl-4-(2-carboxythioxanthen-9-ylidene)piperidine hydrochloride.

| TABLET FORMULA | |
|---|---|
| INGREDIENT | MG. PER TABLET |
| 1-Methyl-4-(2-carboxy-thioxanthen-9-ylidene)piperidine | 1 mg. |
| Calcium phosphate | 52 mg. |
| Lactose | 60 mg. |
| Starch | 10 mg. |
| Magnesium stearate | 1 mg. |

| TABLET FORMULA | |
|---|---|
| INGREDIENT | MG. PER TABLET |
| 1-Methyl-4-(2-carboxyl-thioxanthen-9-ylidene hydrochloride | 1 mg. |
| Calcium phosphate | 53 mg. |
| Lactose | 60 mg. |
| Starch | 10 mg. |
| Magnesium stearate | 1 mg. |

What is claimed is:

1. 1-Methyl-4-(2-carboxy-thioxanthen-9-ylidene)-piperidine or a nontoxic pharmaceutically acceptable salt thereof.

2. A method of treatment of histaminically induced allergies which comprises administering to a patient in need of such treatment an effective amount of 1-methyl-4-(2-carboxy-thioxanthen-9-ylidene)-piperidine or a nontoxic pharmaceutically acceptable salt thereof.

3. A pharmaceutical composition in unit dosage form comprising an appetite stimulant or antihistaminic effective amount of 1-methyl-4-(2-carboxy-thioxanthen-9-ylidene)-piperidine or a nontoxic pharmaceutically acceptable salt thereof and a pharmaceutical carrier therefor.

* * * * *